US012642697B2

(12) United States Patent
Zhang et al.

(10) Patent No.: US 12,642,697 B2
(45) Date of Patent: Jun. 2, 2026

(54) DOUBLE-HEAD SEPARATOR FOR PERIPHERAL ANTERIOR SYNECHIAE

(71) Applicant: Zhongshan Ophthalmic Center of Sun Yat-sen University, Guangzhou (CN)

(72) Inventors: Xiulan Zhang, Guangzhou (CN); Long Wang, Guangzhou (CN); Fengbin Lin, Guangzhou (CN)

(73) Assignee: Zhongshan Ophthalmic Center of Sun Yat-sen University, Guangzhou (CN)

( * ) Notice: Subject to any disclaimer, the term of this patent is extended or adjusted under 35 U.S.C. 154(b) by 272 days.

(21) Appl. No.: 18/492,934

(22) Filed: Oct. 24, 2023

(65) Prior Publication Data

US 2025/0127659 A1 Apr. 24, 2025

(51) Int. Cl.
*A61F 9/007* (2006.01)
*A61B 17/00* (2006.01)
*A61B 17/32* (2006.01)

(52) U.S. Cl.
CPC ..................... *A61F 9/00772* (2013.01); *A61B 2017/00424* (2013.01); *A61B 2017/320044* (2013.01)

(58) Field of Classification Search
CPC .............. A61F 9/00781; A61F 9/00772; A61F 9/0133; A61F 9/013; A61F 11/006; A61B 2017/00424; A61B 17/3211; A61B 2017/00738; A61B 2017/320044; A61B 17/244; A61B 17/24; A61B 2017/320008; A46B 15/0081
See application file for complete search history.

(56) References Cited

U.S. PATENT DOCUMENTS

| | | | | | |
|---|---|---|---|---|---|
| 5,915,433 | A | * | 6/1999 | Hybler | A46B 5/02 15/167.1 |
| 2009/0235474 | A1 | * | 9/2009 | Seigel | A46B 15/0081 15/167.1 |
| 2015/0007402 | A1 | * | 1/2015 | Ladva | A61B 17/244 15/111 |

FOREIGN PATENT DOCUMENTS

| | | | | | |
|---|---|---|---|---|---|
| CN | 202982372 | U | * | 6/2013 | |
| CN | 110742726 | A | * | 2/2020 | ........... A61F 9/0133 |
| CN | 210728011 | U | * | 6/2020 | |
| CN | 216798001 | U | * | 6/2022 | |

* cited by examiner

*Primary Examiner* — Katherine M Shi

(74) *Attorney, Agent, or Firm* — MUNCY, GEISSLER, OLDS & LOWE. P.C.

(57) ABSTRACT

The present invention discloses a double-head separator for peripheral anterior synechiae, including a first head portion, a first neck portion, a handle portion, a second neck portion and a second head portion which are sequentially connected. At least one of the first neck portion and the second neck portion is designed in an elongated shape or designed in a bent structure, at least one of the first head portion and second head portion is provided with an arc-shaped ring in a longitudinal direction substantially perpendicular to the handle portion, and the arc-shaped ring of the first head portion or the second head portion is provided with a plurality of teeth. The separator of the present invention is applicable to various surgery for angle-closure and adherent glaucoma.

19 Claims, 3 Drawing Sheets

DOUBLE-HEAD SEPARATOR FOR PERIPHERAL ANTERIOR SYNECHIAE

TECHNICAL FIELD

The present invention relates to the technical field of surgical instruments, and particularly relates to a double-head separator for peripheral anterior synechiae.

BACKGROUND

Glaucoma is the leading irreversible cause of blindness all over the world. With the increasing development and innovation of the glaucoma diagnosis and treatment technology, glaucoma surgery has gradually changed from traditional filtering surgery, which is complicated to operate and causes more complications, to minimally invasive glaucoma surgery (MIGS), which is easy to operate and causes fewer complications.

Among the others, goniosynechialysis (GSL) is an important technology applied in MIGS for angle-closure glaucoma to separate the peripheral anterior synechiae and unblock the outflow channel for aqueous humor. However, there have been very few surgical instruments specifically used for GSL clinically. Ophthalmologists usually use surgical instruments to operate GSL, such as viscoelastic agents, iris repositors, phaco choppers, intraocular lens alignment hooks. But no matter which kind of instruments are available, it is unable to effectively and conveniently achieve separation for the peripheral anterior synechiae in minimally invasive method, due to its improper angle for holding, improper direction for exerting force, and inadequate iris gripping force, which brings inconvenience for further surgery.

For example, the disadvantages of viscoelastic agent for GSL are: (1) insufficient acting force due to fluidity of the viscoelastic; (2) uncertain effects; (3) easy residues of viscoelastic agent, leading to increase of the intraocular pressure.

The disadvantages of iris repositor for GSL are: (1) bulky structures, causing restricted range of motion in the anterior chamber, which is far from the concept of minimally invasive surgery; (2) not easy to exert force at the root of the iris due to its flatness and smoothness.

The disadvantages of phaco chopper for GSL are: (1) easy to injure the iris due to its relatively sharp head, causing tearing or bleeding of the iris; (2) smaller separation range at one time because of narrow width of its head, causing lower separation efficiency; (3) lower gripping force because of its smoothness when horizontally entering anterior chamber for separation on the surface of the peripheral iris, further resulting in lower separation efficiency; (4) inconvenient operation as the direction for exerting force by the wrist of the ophthalmologists does not conform to the requirements of the ergonomics; (5) not enough room for separating in the rightward direction, making operation much more inconvenient.

The disadvantage of intraocular lens alignment hooks for GSL is undesirable separation effect due to its blunt head as iris has high retractility.

It is therefore desirable to provide a specialized separator for the peripheral anterior synechiae under direct vision as an important practical tool for effectively separating the peripheral anterior synechiae in glaucoma surgery.

SUMMARY

The present invention therefore seeks to provide a double-head separator for peripheral anterior synechiae, which is applicable to various surgery for angle-closure and adherent glaucoma, and is capable of improving surgical efficiency and thus achieving high safety and operability.

According to the present invention, a double-head separator for peripheral anterior synechiae includes a first head portion, a first neck portion, a handle portion, a second neck portion and a second head portion connected in sequence, wherein at least one of the first neck portion and the second neck portion is designed in an elongated shape or in a bent structure, and at least one of the first head portion and second head portion is provided with an arc-shaped ring in the longitudinal direction substantially perpendicular to the handle portion. In addition, the arc-shaped ring of the first head portion or the second head portion is provided with a plurality of teeth.

According to the separator of the present invention, the handle portion makes easy for a doctor to grasp for surgery, the first neck portion in the elongated shape or the bent structure is better applicable to cornea limbus incisions in different portions, thus allowing the separator in higher practicability, and the arc-shaped ring on the head portion can facilitate separating the peripheral anterior synechiae and facilitate entering or exiting the anterior chamber, thereby improving surgical efficiency.

In the present invention, the surface of the arc-shaped ring is preferably of a smooth structure, which can better fit the corneal limbus curvature, particularly suitable for carrying out separation at the left and right sides of the peripheral anterior synechiae in a wide range. Such arc-shaped ring is more suitable for separating the peripheral anterior synechiae with slight adhesion and a higher risk of hemorrhage or iris damage, and thus achieving higher safety and higher operability for surgery.

In the present invention, the second neck portion can also be designed as the elongated shape or the bent structure. In order to facilitate operation or surgery, in the case that the second neck portion is designed as the bent structure, the first neck portion can be of the elongated shape or the bent structure, such construction facilitates use for the doctors. In addition, by providing the teeth on the arc-shaped ring of the first head portion or the second head portion, the peripheral anterior synechiae in different cases can be better separated. Specifically, the separator with teeth is particularly suitable for separating the peripheral anterior synechiae that is more tightly adhered or more difficult to separate.

According to one embodiment of the double-head separator of the present invention, in the case that the first neck portion and the second neck portion are both designed in form of the bent structure, the bent structures of the first neck portion and the second neck portion are oriented in opposite directions.

Preferably, in the case that the first neck portion and the second neck portion are both designed as the elongated shape or the bent structure, the first neck portion are provided in central symmetry and thus completely overlaps with the second neck portion when the first neck portion is rotated 180 degrees around the center point of the handle portion. Specifically, when both the first neck portion and the second neck portion are in the elongated shape, both of them are also of an axisymmetric structure with the center-line of the handle portion as the axis; while when both the first neck portion and the second neck portion are in the bent structure, the bent structures of the second neck portion and the first neck portion are preferably oriented in opposite directions, such configuration is more convenient to use.

According to the present invention, the teeth are provided on the arc-shaped ring towards to the corresponding neck portion, and the teeth has length of 0.05-0.2 mm and are inclined relative to the corresponding neck portion at an angle of 10-20°.

More preferably, the teeth have length of 0.1 mm. The teeth may be designed as a cylindrical structure with the dimension of the length, width, and height of 0.1×0.1×0.1 mm, and the bottom of the teeth is in an arc-shaped shape for better separating the peripheral anterior synechiae with less injuries thereto.

More preferably, the teeth are inclined relative to the corresponding neck portion at an angle of 15°, such inclined design can facilitate downwardly and backwardly applying an acting force during operation, as well as reducing disturbance or scratches on the posterior lip of a corneal incision when entering or exiting the corneal incision conveniently.

According to the present invention, the total length of the arc-shaped ring is 0.8-1.5 mm, the diameter of the arc-shaped ring is 0.1-0.3 mm, and preferably four to six the teeth are uniformly provided on the arc-shaped ring.

More preferably, the total length of the arc-shaped ring is 1 mm, and the diameter of the arc-shaped ring is 0.2 mm. The arc-shaped ring is provided perpendicular to the first neck portion/second neck portion at the connection therewith, and the number of the teeth of the arc-shaped ring is four to six. In the present invention, the teeth can give the iris a better gripping force, thus achieving better separation for the peripheral anterior synechiae.

According to the double-head separator of the present invention, the first neck portion/second neck portion designed in the bent structure is provided with a bending portion, and the bending angle of the bending portion is 140-150°.

More preferably, the bending angle of the bending portion is 145°. With the bending portion on the first neck portion/second neck portion, the separator can be effectively applied to an upper corneal incision, and proper bending angle can also effectively circumvent the influence of the eyelid as well as the high nose bridge.

Particularly, the first neck portion/second neck portion is divided into a straight portion and an inclined portion by the bending portion, the straight portion is connected to the handle portion, the inclined portion is connected to the first head portion/second head portion. The length of the straight portion is preferably 6-8 mm and the length of the inclined portion is preferably 9-11 mm according to the present invention.

More preferably, the length of the straight portion is 7 mm and the length of the inclined portion is 10 mm.

According to the double-head separator of the present invention, the length of the first neck portion/second neck portion designed in the elongated shape is 15-20 mm.

The first neck portion/second neck portion designed in the elongated shape is particularly suitable for bitamporal and supratemporal incisions, which facilitates directly entering the anterior chamber to reach the opposite anterior chamber angle for operation under direct vision of a microscope, without other auxiliary tools.

More preferably, the length of the first neck portion/second neck portion designed in the elongated shape is particularly 17 mm.

According to the double-head separator of the present invention, the diameter of the first neck portion/second neck portion is smaller than the diameter of the handle portion.

According to the double-head separator of the present invention, the handle portion, the first neck portion, the second neck portion, the first head portion, the second head portion and the blunt teeth may be integrally formed.

The separator with integrally formed structure may have better transition and thus does not require other auxiliary accessories during operation, thereby achieving safer and more convenient use.

According to the double-head separator of the present invention, the length of the handle portion is preferably 135-140 mm, the middle portion of the handle portion is designed in a cylindrical structure and the two end portions of the handle portion are designed in a conical structure.

More preferably, the length of the handle portion is 138 mm. Such length of the handle portion is in accordance with the requirements of the ergonomics and is more convenient to exert force by the wrist and fingers of the operators.

Preferably, the separator of the present invention is made of a stainless-steel material, which facilitates sterilization at high temperature and reuse, thus reducing the waste of medical consumables.

Compared with the prior art, with the arc-shaped ring on the first head portion in the present invention, it is more suitable for separating the peripheral anterior synechiae with slight adhesion and a higher risk of hemorrhage or iris damage; with the teeth on the arc-shaped ring of the first head portion/second head portion, it is more suitable for separating the peripheral anterior synechiae that is more tightly adhered and more difficult to separate; with the first neck portion/second neck portion designed in the elongated shape, it is more suitable for bitamporal and supratemporal incisions, facilitating directly entering the anterior chamber to reach the anterior chamber angle for operation under direct vision of a microscope; and the bending structure of the first neck portion/second neck portion makes the separator more applicable to a corneal incision above the nose so as to circumvent the influence of the eyelid as well as the high nose bridge. Therefore, the separator of the present invention is applicable to various surgery for angle-closure and adherent glaucoma, and has the advantageous effects of higher applicability, better safety, and higher operation efficiency, which is more in line with the needs of users.

DETAILED DESCRIPTION

Figure 1:
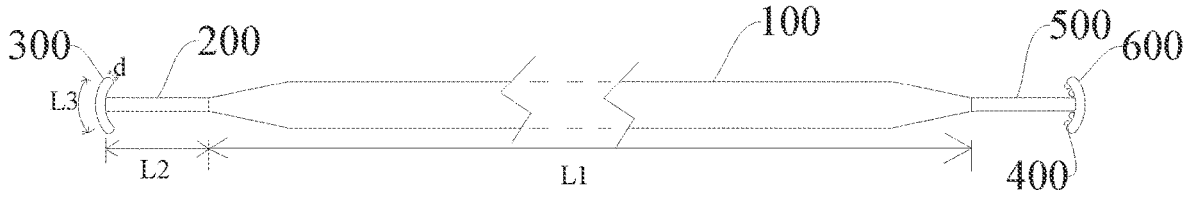
FIG. 1 is a structural schematic view of a separator according to an embodiment of the present invention.

The accompanying drawings are for exemplary illustration only, and should not be construed as limitations on the present invention. In order to better illustrate the following embodiment, some parts in the accompanying drawings may be omitted, enlarged or reduced, and they do not represent the size of the actual product. For those skilled in the art, it is understandable that certain well-known structures and descriptions thereof in the drawings may be omitted.

Referring to FIG. 1, a double-head separator for peripheral anterior synechiae is provided according to an embodiment, including a first head portion 300, a first neck portion 200, a handle portion 100, a second neck portion 500 and a second head portion 600 which are sequentially connected. In order to conforms to the requirements of the ergonomics, the middle portion of the handle portion 100 is formed in a cylindrical shape. Such configuration is advantageous for the wrist or fingers of the ophthalmologists to exert force conveniently. While the both two end portions of the handle portion 100 are formed in a conical shape, which is better to respectfully connect the first neck portion 200 and the second neck portion 500. In this embodiment, the length L1 of the handle portion 100 is particularly 138 mm. However, in the context of the present invention, the length L1 of the handle portion 100 is preferably 135-140 mm.

According to the present embodiment, the first neck portion 200 is preferably in form of elongated shape. In this way, the separator can directly enter the anterior chamber to reach the opposite anterior chamber angle for operation under direct vision of a microscope. In the present embodiment, the length L2 of the first neck portion 200 is particularly 17 mm. However, in the context of the present invention, the length L2 of the first neck portion 200 is preferably 15-20 mm.

The first head portion 300 in this embodiment is provided with an arc-shaped ring in the longitudinal direction, which has a smooth surface and with two ends thereof smoothly transited. The whole arc-shaped ring thus is of a cylindrical structure with a radian, the arc length L3 thereof is preferably 1 mm, the diameter d of the cylindrical structure is preferably 0.2 mm, namely the width of the ring is 0.2 mm. However, in the context of the present invention, the arc length L3 of the arc-shaped ring is 0.8-1.5 mm and the diameter d of the cylindrical structure is 0.1-0.3 mm. In the present embodiment, the arc-shaped ring is perpendicular to the first neck portion 200 at the connection with the first neck portion 200 to make the sides of the arc-shaped ring stressed more uniformly. The arc-shaped ring can facilitate separating the peripheral anterior synechiae and is particularly suitable for separating the peripheral anterior synechiae with slight adhesion and higher risk of hemorrhage or iris damage.

In this embodiment, the second neck portion 500 has same structure with the first neck portion 200, and the second neck portion 500 and the first neck portion 200 are symmetrically arranged relative to the centerline of the handle portion 100. Except that, the arc-shaped ring of the second head portion 600 in this embodiment is further provided with a plurality of teeth 400, such teeth 400 can be integrally formed with the arc-shaped ring and together forming the second head portion 600 of the separator. The teeth 400 are designed in a cylindrical form towards the second neck portion 500 in the present embodiment, and the bottom of the teeth 400 is smoothly transited in an arc-shaped shape, which is better suitable for separating the peripheral anterior synechiae with less damage thereto. Preferably, the dimension of the length, width and height of each tooth 400 in this embodiment is 0.1×0.1×0.1 mm.

Figure 2:
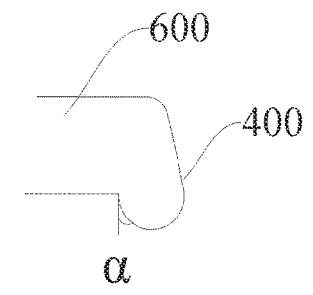
FIG. 2 is a horizontal side view of teeth in FIG. 1.

According to the present embodiment, the teeth 400 are obliquely provided on the arc-shaped ring relative to the second neck portion 500 with an inclination angle α of 15° as shown in FIG. 2. However, in the context of the present invention, the inclination angle α is preferably 10-20°. Such configuration can facilitate especially downwardly and backwardly applying an acting force, as well as conveniently entering or exiting the corneal incision with less disturbance or scratches on the posterior lip of the corneal incision.

In the present embodiment, the number of the teeth 400 is preferably five, which are uniformly provided on the arc-shaped ring. Five blunt teeth 400 can give the iris a better gripping force while realizing effective separation of the peripheral anterior synechiae.

The handle portion 100, the first neck portion 200, the first head portion 300, the second neck portion 500, the second head portion 600, and the teeth 400 in this embodiment can be integrally formed, and preferably made of stainless-steel material. Due to the arrangement of the integrally formed structure, it is more conducive to mass production, and there is no need for other auxiliary tools, thereby achieving higher safety and better operability. The stainless-steel material facilitates sterilization at high temperature to reuse, thus reducing the waste of medical consumables.

Specifically, the separator for the peripheral anterior synechiae in this embodiment can be used in surgery, especially goniosynechialysis, according to the following operation method:

S1) the separator for the peripheral anterior synechiae is sterilized with high-pressure steam; and S2) under a microscope, a gonioscope is hold in one hand of an operator for auxiliary observation, and the separator is hold in the other hand to enter the anterior chamber and reach to the opposite anterior chamber angle to be separated, making the head portion of the separator lying on the root of the iris, and acting force is applied especially downwardly and backwardly to separate the peripheral anterior synechiae.

Figure 3:
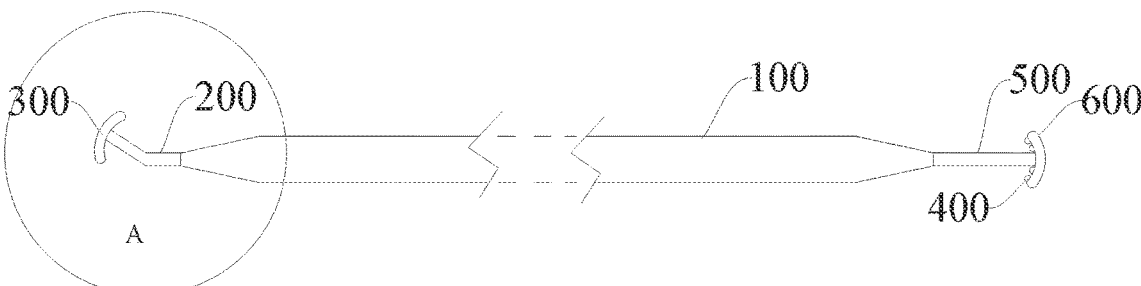
FIG. 3 is a structural schematic view of a separator according to another embodiment of the present invention.
Figure 4:
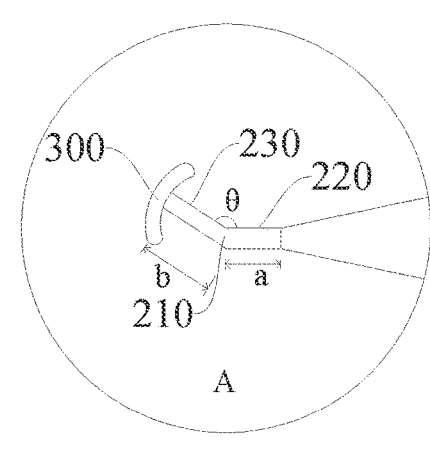
FIG. 4 is an enlarged view of part A in FIG. 2.

With reference to FIG. 3 and FIG. 4, the first neck portion 200 of the separator in this embodiment is designed in a bent structure, specifically, having a bending portion 210, and the first neck portion 200 is divided into a straight portion 220 and an inclined portion 230 by the bending portion 210. The straight portion 220 is connected to the handle portion 100 and the inclined portion 230 is connected to the first head portion 300. More preferably, the length a of the straight portion 220 is 7 mm, the length b of the inclined portion 230 is 10 mm, and the bending angle θ formed by the bending portion 210 is 145°, namely the angle between the straight portion 220 and the inclined portion 230 is 145°. However, in the context of the present invention, the length of the straight portion is preferably 6-8 mm, the length of the inclined portion is preferably 9-11 mm, and the bending angle of the bending portion is 140-150°. With the bent structure of the first neck portion 200, it is more favorable to circumvent the influence of the eyelid and the high nose bridge. Such bent structure of the first neck portion 200 is particularly suitable for the anterior chamber angle at the upper corneal incision.

Figure 5:
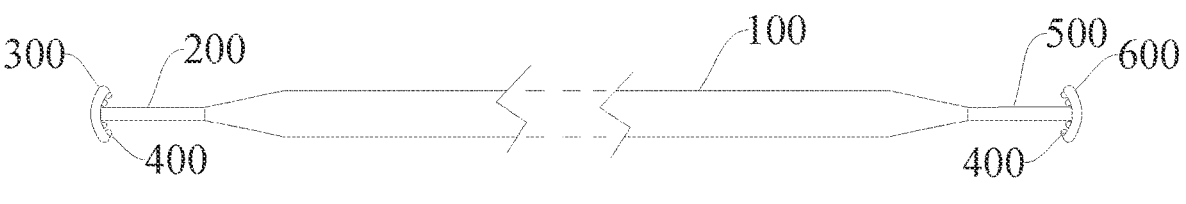
FIG. 5 is a structural schematic view of a separator according to another embodiment of the present invention.

Referring now to FIG. 5, the arc-shaped ring of the first head portion 300 in this embodiment is also provided with a plurality of teeth 400, such teeth 400 can be integrally formed with the arc-shaped ring, and together forming the first head portion 300 of the separator. The teeth 400 of the first head portion 300 are designed in a cylindrical structure towards the first neck portion 200, which is better suitable for separating the peripheral anterior synechiae with less injuries to the anterior chamber angle. Preferably, the dimension of the length, width and height of the teeth 400 of the first head portion 300 is also 0.1×0.1×0.1 mm.

Figure 6:
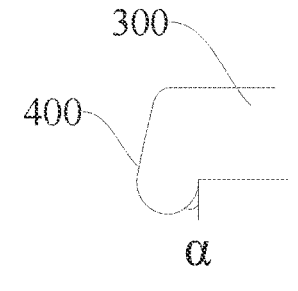
FIG. 6 is a horizontal side view of teeth in FIG. 5.

In this embodiment, the teeth 400 of the first head portion 300 are also obliquely provided on the arc-shaped ring relative to the first neck portion 200 with an inclination angle α of 15° as shown in FIG. 6. Such configuration can facilitate especially downwardly and backwardly applying an acting force, as well as conveniently entering or exiting the corneal incision with less disturbance or scratches on the posterior lip of the corneal incision.

Similar to the second head portion 600, five teeth 400 are provided on the first head portion 300 in this embodiment, which are uniformly arranged on the arc-shaped ring of the first head portion 300. Five teeth 400 can give the iris a better gripping force while realizing effective separation of the peripheral anterior synechiae.

That is, the separator in this embodiment is axisymmetric.

Figure 7:
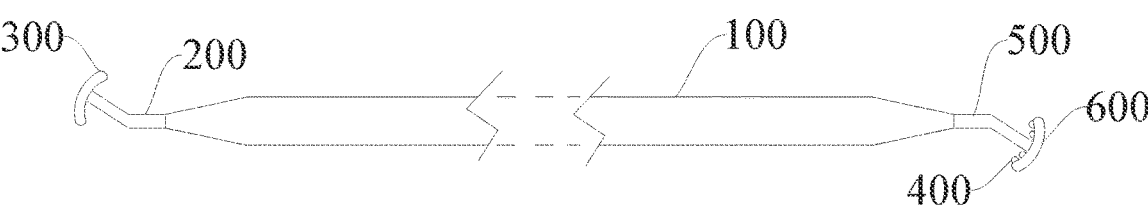
FIG. 7 is a structural schematic view of a separator according to another embodiment of the present invention.

Referring to FIG. 7, the first neck portion 200 and the second neck portion 500 in this embodiment are both designed in a bent structure, and the first neck portion 200 completely overlaps with the second neck portion 500 after the first neck portion 200 is rotated 180 degrees on the handle portion 100 around the center of the handle portion 100. That is, the first neck portion 200 and the second neck portion 500 are provided in central symmetry, namely, the bent structures of the first neck portion 200 and the second neck portion 500 in this embodiment are oriented in opposite directions.

Specifically, in this embodiment, the first neck portion 200 and the second neck portion 500 are each provided with a bending portion which divides the first neck portion 200/second neck portion 500 into a straight portion and an inclined portion, wherein the straight portion is connected to the handle portion 100 and the inclined portion is connected to the first head portion 300/second head portion 600. More preferably, the length of the straight portion is 7 mm, the length of the inclined portion is 10 mm, and the bending angle formed by the bending portion is 145°. With the bent structure of the first neck portion 200/second neck portion 500, it is more favorable to circumvent the influence of the eyelid and the high nose bridge. Such bent structure of the first neck portion 200/second neck portion 500 is particularly suitable for the anterior chamber angle at the upper corneal incision.

Figure 8:
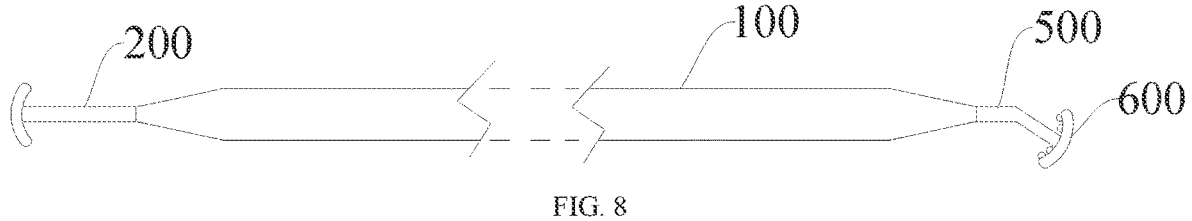
FIG. 8 is a structural schematic view of a separator according to another embodiment of the present invention.

With reference to FIG. 8, in this embodiment, only the second neck portion 500 is designed as a bent structure. Specifically, the second neck portion 500 is provided with a bending portion which divides the second neck portion 500 into a straight portion connected to the handle portion 100 and an inclined portion connected to the second head portion 600. More preferably, the length of the straight portion is 7 mm, the length of the inclined portion is 10 mm, and the bending angle formed by the bending portion is 145°. With the bent structure of the second neck portion 500, it is more favorable to circumvent the influence of the eyelid and the high nose bridge. Such bent structure of the second neck portion 500 is particularly suitable for the anterior chamber angle at the upper corneal incision.

Figure 9:
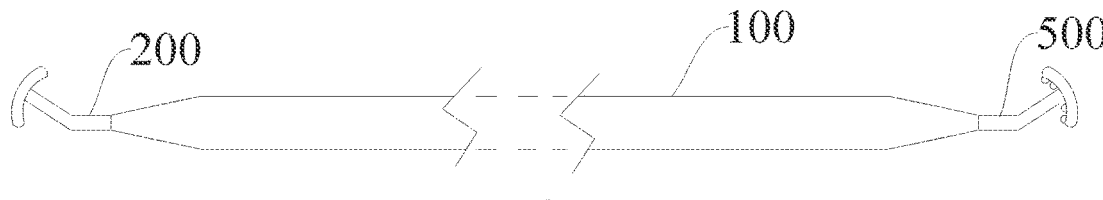
FIG. 9 is a structural schematic view of a separator according to another embodiment of the present invention.

With reference to FIG. 9, the first neck portion 200 and the second neck portion 500 in this embodiment are both designed as a bent structure, and the bent structures of the first neck portion 200 and the second neck portion 500 in this embodiment are provided in axial symmetry with the centerline of the handle portion 100. That is, the bent structures of the first neck portion 200 and the second neck portion 500 in this embodiment are oriented in the same direction. The whole separator in this embodiment is in axial symmetry.

Obviously, the above-mentioned embodiments of the present invention are only examples for clearly illustrating the technical solution of the present invention, rather than limiting the embodiments of the present invention. Any modifications, equivalent replacements and improvements made within the spirit and principles of claims of the present invention shall be included within the protection scope of the claims of the present invention.

What is claimed is:

1. A double-head separator for peripheral anterior synechiae, comprising a first head portion, a first neck portion, a handle portion, a second neck portion, and a second head portion, which are sequentially connected, wherein at least one of the first neck portion and the second neck portion is designed in an elongated shape or designed in a bent structure, and at least one of the first head portion and second head portion is provided with an arc-shaped ring in a longitudinal direction substantially perpendicular to the handle portion, and the arc-shaped ring of the first head portion or the second head portion is provided with a plurality of teeth, and wherein the plurality of teeth are provided on the arc-shaped ring toward to the corresponding neck portion, and each of the teeth has a length of 0.05-0.2 mm and is inclined relative to the corresponding neck portion at an angle of 10-20°.

2. The double-head separator according to claim 1, wherein the first neck portion and the second neck portion are both designed in the bent structure, and the bent structures of the first neck portion and the second neck portion are oriented in opposite directions.

3. The double-head separator according to claim 1, wherein a total length of the arc-shaped ring is 0.8-1.5 mm, a diameter of the arc-shaped ring is 0.1-0.3 mm, the number of the teeth provided on the arc-shaped ring is four to six, and the teeth are uniformly provided on the arc-shaped ring.

4. The double-head separator according to claim 1, wherein at least one of the first neck portion and the second neck portion designed in the bent structure is provided with a bending portion, and a bending angle of the bending portion is 140-150°.

5. The double-head separator according to claim 4, wherein at least one of the first neck portion and the second neck portion is divided into a straight portion connected to the handle portion and an inclined portion connected to the corresponding head portion by the bending portion.

6. The double-head separator according to claim 5, wherein a length of the straight portion is 6-8 mm and a length of the inclined portion is 9-11 mm.

7. The double-head separator according to claim 1, wherein a length of at least one of the first neck portion and the second neck portion designed in the elongated shape is 15-20 mm.

8. The double-head separator according to claim 1, wherein a diameter of at least one of the first neck portion and the second neck portion is smaller than a diameter of the handle portion.

9. The double-head separator according to claim 1, wherein the handle portion, the first neck portion, the second neck portion, the first head portion, the second head portion and the teeth are integrally formed.

10. The double-head separator according to claim 1, wherein a length of the handle portion is 135-140 mm.

11. The double-head separator according to claim 1, wherein a middle of the handle portion is designed in a cylindrical structure, and two end portions of the handle portion are designed in a conical structure.

12. A double-head separator for peripheral anterior synechiae, comprising a first head portion, a first neck portion, a handle portion, a second neck portion, and a second head portion, which are sequentially connected, wherein at least one of the first neck portion and the second neck portion is designed in a bent structure, and at least one of the first head portion and second head portion is provided with an arc-shaped ring in a longitudinal direction substantially perpendicular to the handle portion, and the arc-shaped ring of the first head portion or the second head portion is provided with a plurality of teeth, and wherein at least one of the first neck portion and the second neck portion is provided with a bending portion, and a bending angle of the bending portion is 140-150°.

13. The double-head separator according to claim 12, wherein at least one of the first neck portion and the second neck portion is divided into a straight portion connected to the handle portion and an inclined portion connected to the corresponding head portion by the bending portion.

14. The double-head separator according to claim 13, wherein a length of the straight portion is 6-8 mm and a length of the inclined portion is 9-11 mm.

15. The double-head separator according to claim 12, wherein a length of the handle portion is 135-140 mm.

16. The double-head separator according to claim 12, wherein a middle of the handle portion is designed in a cylindrical structure, and two end portions of the handle portion are designed in a conical structure.

17. A double-head separator for peripheral anterior synechiae, comprising a first head portion, a first neck portion, a handle portion, a second neck portion, and a second head portion, which are sequentially connected, wherein at least one of the first neck portion and the second neck portion is designed in an elongated shape, and at least one of the first head portion and second head portion is provided with an arc-shaped ring in a longitudinal direction substantially perpendicular to the handle portion, and the arc-shaped ring of the first head portion or the second head portion is provided with a plurality of teeth, and wherein a length of at least one of the first neck portion and the second neck portion is 15-20 mm.

18. The double-head separator according to claim 17, wherein a length of the handle portion is 135-140 mm.

19. The double-head separator according to claim 17, wherein a middle of the handle portion is designed in a cylindrical structure, and two end portions of the handle portion are designed in a conical structure.

* * * * *